United States Patent [19]

Mathew

[11] Patent Number: 5,026,918

[45] Date of Patent: Jun. 25, 1991

[54] SYNTHESIS OF 2,3,5-TRISUBSTITUTED-2-CYCLOPENTE-NONES VIA BASE INDUCED CYCLIZATION OF ALPHA-CHLORO UNSATURATED KETONES

[75] Inventor: Jacob Mathew, Fenton, Mo.

[73] Assignee: Petrolite Corporation, St. Louis, Mo.

[21] Appl. No.: 515,299

[22] Filed: Apr. 27, 1990

[51] Int. Cl.$^5$ .............................................. C07C 45/65
[52] U.S. Cl. ..................................... 568/348; 568/316
[58] Field of Search ................................ 568/348, 316

[56] References Cited

U.S. PATENT DOCUMENTS 3,983,175  9/1976  Tamai et al. ...................... 568/348
4,371,711  2/1983  Saito et al. ........................ 568/348

FOREIGN PATENT DOCUMENTS 53-149952  12/1978  Japan .................................. 568/348

OTHER PUBLICATIONS

R. A. Ellison, Synthesis, 1973, 397.
M. Mikolajcayk, S. Grzejsczak, & K. Korbacz, Tetrahedron Lett. 22, 3097 (1981).
M. Miklojczyk, S. Grzejsczak, & P. Kyzawa, Tetrahedron Lett., 23, 2237 (1982).
J. L. Herrmann, J. E. Richman, & R. H. Schlessinger, Tetrahedron Lett., 35, 3275 (1973).
P. Bakuzis & M. L. F. Bakuzis, J. Org. Chem. 42, 2362 (1977).
S. C. Subramaniam, P. J. Thomas, V. R. Mamdapur, & M. S. Chadha, J. Chem. Soc. Perkin 1,2346 (1979).
A. G. Cameron & A. T. Hewson, J. Chem. Soc. Perkin. Trans. 1,2979 (1983).
I. Kawamoto, S. Muramatsu, & Y. Yura, Tetrahedron Lett. 48, 4223 (1974).
Y. Yura & J. Ide, Chem. Pharm. Bull, 17, 408 (1969).
J. L. E. Erickson & F. E. Collins, Jr., J. Org. Chem. 30, 1050 (1965).
K. Sisido, S. Torji, & M. Kawanisi, J. Org. Chem., 29, 904 (1964).
G. Buchi & B. Egger, J. Org. Chem., 36, 2021 (1971).
S. C. Welch, J. N. Assercq, J. P. Loh, & S. A. Glase, J. Org. Chem. 52, 1440 (1987).
P. Grieco, J. Org. Chem., vol. 37, No. 14, 2363 (1972).
T. Mukaiyama, J. Am. Chem. Soc., 94:24 (1972), pp. 8641-8642.
H. O. House, C. Chu, J. M. Wilkins, and M. J. Umen, J. Org. Chem., vol. 40, No. 10, p. 1460, (1975).

*Primary Examiner*—James H. Reamer
*Attorney, Agent, or Firm*—Jeffrey S. Boone; Stanley M. Tarter; Kenneth Solomon

[57] ABSTRACT

2,3,5-trisubstituted-2-cyclopentenones or 2,3-disubstituted-2-cyclopentenones (such as cis-jasmone) are prepared by contacting a 3-chloro-3,4-disubstituted-4-pentene-2-one with a strong base. Methods of preparing the reactants are also disclosed.

21 Claims, No Drawings

SYNTHESIS OF 2,3,5-TRISUBSTITUTED-2-CYCLOPENTENONES VIA BASE INDUCED CYCLIZATION OF ALPHA-CHLORO UNSATURATED KETONES

BACKGROUND OF THE INVENTION

This invention relates to a new method for the synthesis of 2,3,5-trisubstituted-2-cyclopentenones. In particular, the invention relates to such a method using a base induced cyclization.

2,3,5-trisubstituted-2-cyclopenteones (and 2,3-disubstituted-2-cyclopentenones) are useful as fragrances and as pharmaceutical intermediates. For instance, 2-(cis-2-pentenyl)-3-methyl-2-cyclopentenone, commonly known as cis-jasmone, and 2-pentyl-3-methyl-2-cyclopentenone, commonly known as dihydrojasmone, are expensive perfume ingredients, and 2,3-dimethyl-2-cyclopentenone is an intermediate useful in the synthesis of the antibiotic methylenomycin B.

2,3,5-trisubstituted-2-cyclopentenones have been prepared by the intramolecular base catalyzed aldolcondensation of acyclic 1,4-dicarbonyl compounds (R. A. Ellison, Synthesis, 1973, 397; M. Mikolajcayk, S. Grzejsczak, and K. Korbacz, Tetrahedron Lett., 22, 3097 (1981); M. Miklojczyk, S. Grzejsczak, and P. Kyzawa, Tetrahedron Lett., 23, 2237 (1982); J. L. Herrman, J. E. Richmann, and R. H. Schlessinger, Tetrahedron Lett., 35, 3275 (1973); P. Bakuzis and M. L. F. Bakuzis, J. Org. chem. 42, 2362 (1977); S. C. Subramaniam, P. J. Thomas, V. R. Mamdapur, and M. S. Chadha, J. Chem. Soc. Perkin 1, 2346 (1979)), and by an intramolecular Wittig reaction effected by the treatment of the anion of α-diketones with vinyl triphenyl phosphonium salts (A. G. Cameron and A. T. Hewson, J. Chem. Soc. Perkin. Trans. 1, 2979 (1983); I. Kawamoto, S. Muramatsu, and Y. Yura, Tetrahedron Lett. 48, 4223 (1974)). Other routes based on dioxocyclopentanes (Y. Yura and J. Ide, Chem. Pharm. Bull, 17, 408 (1969)), cyclopentane-1,2-diones (J. L. E. Erickson and F. E. Collins, Jr., J. Org. Chem. 30, 1050 (1965)) and cyclodehydration of γ-lactones (K. Sisido, S. Torji, and M. Kawanisi, J. Org. Chem., 29, 904 (1964)), but these routes tend to be either very lengthy or involve the use of very expensive reagents. Other routes include (G. Buchi and B. Egger, J. Org. Chem., 26, 2021 (1971); S. C. Welch, J. N. Assercq, J. P. Loh, and S. A. Glase, J. Org. Chem., 52, 1440 (1987); P. Grieco, J. Org. Chem., Vol. 37, No. 14, (1972) p. 2363–2364; and T. Mukaiyama, J. Am. Chem. Soc., 94:24 (1972) p. 8641–8642).

SUMMARY OF THE INVENTION

Briefly, the invention comprises a novel method of preparing known 2,3,5-trisubstituted-2-cyclopentenones (or 2,3-disubstituted-2-cyclopentenones) from a 3-chloro-3,4-disubstituted-4-pentene-2-one and a base.

The method of the invention is particularly easy and inexpensive to carry out and produces valuable products in good yield.

DETAILED DESCRIPTION OF THE INVENTION

In this specification and claims, numerical values are not critical unless otherwise stated. That is, the numerical values may be read as if they were prefaced with the words "about" or "substantially".

The invention is concerned with the synthesis of 2, 3, 5-trisubstituted-2-cyclopentenones having the general formula:

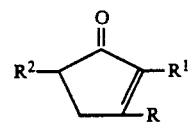
(I)

wherein R is an organic moiety, generally an aryl, alkyl, or alkenyl, desirably an alkyl, more desirably a $C_1$ to $C_{32}$ alkyl, preferably a $C_1$ to $C_{12}$ alkyl, more preferably a $C_1$ to $C_8$ alkyl, and most preferably a $C_1$ alkyl moiety; $R^1$ is an organic moiety, generally an aryl, alkyl, or alkenyl, desirably a $C_1$ to $C_{32}$ alkyl or $C_2$ to $C_{32}$ alkenyl, more desirably a $C_1$ to $C_{12}$ alkyl or $C_2$ to $C_{12}$ alkenyl, preferably a $C_1$ to $C_8$ alkyl or $C_2$ to $C_8$ alkenyl, and most preferably a methyl, pentyl, or cis 2-pentenyl moiety; and $R^2$ is H or $C_1$ to $C_{12}$ hydrocarbon moiety, desirably H or a $C_1$ to $C_{12}$ alkyl moiety, more desirably H or $C_1$-$C_6$ alkyl moiety, preferably H or a $C_1$ to $C_3$ alkyl moiety, more preferably H or $CH_3$, and most preferably H. Preferred species include 2-(cis-2-pentenyl)-3-methyl-2-cyclopentenone (cis-jasmone), 2-pentyl-3-methyl-2-cyclopentenone (dihydrojasmone), and 2,3-dimethyl-2-cyclopentenone.

One compound used in the process of the invention is a 3-chloro-3,4-disubstituted-4-pentene-2-one. Such compounds have the general formula:

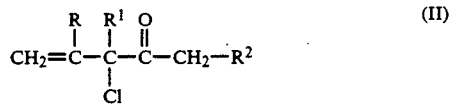
(II)

wherein R, $R^1$, and $R^2$ are as defined above.

3-chloro-3,4-disubstituted-4-pentene-2-ones may be conveniently prepared by the reaction of a 3,4-disubstituted-3-pentene-2-one of the formula:

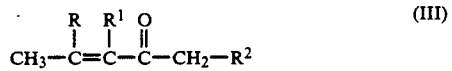
(III)

wherein R, $R^1$, and $R^2$ are as defined above, with an acidified halogen such as that produced by a mixture of $Ca(OCl)_2$ and ethanoic acid in a two phase system of water and dichloromethane, generally following the method of Wolinsky and coauthors in Tetrahedron Lett., 1981, 5019; and Tetrahedron Lett., 1980, 441; both of which are incorporated herein by reference.

The 3,4-disubstituted-3-pentene-2-ones useful in the invention are either commercially available or can be readily prepared by one skilled in the art using conventional technology. The examples illustrate several such preparations.

The method of the invention is carried out by subjecting the 3-chloro-3,4-disubstituted-4-pentene-2-one to a strong base which will effect the ring closure to form a cyclopenteneone. In qeneral, by the term "strong base" is meant any base capable of effecting the cyclization reaction. Four preferred based are:

A. Ammonium hydroxide;
B. An alkali metal hydroxide and a phase transfer catalyst;
C. Alkali metal alkoxides; or

D. Alkyl lithium amines.

Ammonium hydroxide can be used by simply blending an excess amount with the penteneone at room temperature. The reaction will take place in 1 to 24 hours. Because of its low cost and ease of use, ammonium hydroxide is a particularly preferred base.

An alkali metal hydroxide such as potassium hydroxide or preferably sodium hydroxide can be used alone as a base, but the reaction rate is so slow as to be commercially impractical. However, with the addition of a phase transfer catalyst it becomes much more active. Suitable phase transfer catalysts include triethyldodecyl ammonium chloride. The sodium hydroxide and phase transfer catalyst can be mixed with the penteneone at room temperature for 1 to 8 hours.

Alkali metal alkoxides are used by simply mixing with the penteneone at a convenient temperature of illustratively 0° C. to 100° C., with ambient conditions being exemplary. The preferred alkali metal alkoxide is potassium t-butoxide (also known as potassium t-butylate).

Alkyl lithium amines can be prepared in situ by blending an alkyl amine and an alkyl lithium compound. For instance, di-isopropyl amine and n-butyl lithium can be blended to transfer the lithium atom to the amine compound where it will replace a hydrogen. The lithium-amine compound can then, without separation from the reactants and byproducts, be used directly by blending with the penteneone at temperatures exemplified by 0° C. to room temperature.

No matter which base is used, the cyclopentenone formation can be verified by spectral analysis and purification may take place by chromatography (for small scale batches) or distillation (more appropriate for commercial quantities).

The process of the invention is particularly suitable for the manufacture of relatively high value products such as perfume ingredients (cis-jasmone and dihydrojasmone) and antibiotics (methyleneomycin-B), and the synthesis of these compounds is shown in the examples.

EXAMPLES 1–3

2,3,5-trimethyl-2-cyclopentene-1-one

EXAMPLE 1

Precursor Formation

Step A 3-methyl-2-butene was reacted with 1-chloropropanal in the presence of stannous chloride, using conventional techniques (see H. O. House, C. Chu, J. M. Wilkins, and M. J. Umen, *J. Org. Chem.*, Vol. 40, No. 10, p. 1460, 1975), to produce 4,5-dimethyl-4-hexene-3-one:

$$CH_3-C(CH_3)=C(CH_3)-C(O)-CH_2-CH_3$$

Step B 6.5 g (50 millimole) of the product of Step A was dissolved in 250 ml of CH$_2$Cl$_2$ and 25 ml of water. The solution was cooled to 0° C. and 5.5 g (25 millimole) of a 66% active calcium hypochlorite (Ca(OCl)$_2$) was added with stirring. 3 g (50 millimole) of glacial acetic acid was added dropwise over 5 minutes. 20 minutes later the mixture was diluted with 100 ml of water and the CH$_2$Cl$_2$ layer was washed with 5% sodium bicarbonate and water. Drying over magnesium sulfate yielded 7 g (68% yield) of a pale yellow oil identified as 4-chloro-4,5-dimethyl-5-hexene-3-one:

$$CH_2=C(CH_3)-C(CH_3)(Cl)-C(O)-CH_2-CH_3$$

EXAMPLE 2

Invention 1.6 g (10 millimole) of the product of Example 1 was dissolved in 1 ml of tetrahydrofuran, and 30 ml of 28% NH$_4$OH was then added. The mixture was stirred for 12 hours at room temperature. Dilution with 20 ml of water and extraction with two 15 ml quantities of ether yielded, after evaporation of solvent, a crude yellow oil. Purification by flash column chromatography yielded 0.9 g (74% yield) of a yellow oil identified as 2,3,5-trimethyl-2-cyclopentene-1-one:

[structure of 2,3,5-trimethyl-2-cyclopentene-1-one]

EXAMPLE 3

Invention 1.6 g (10 millimole) of the product of Example 1 was dissolved in 10 ml of tetrahydrofuran. 100 mg of tetrabutyl ammonium bromide was added, followed by the addition over 5 minutes of 2 ml of 4N NaOH in 5 ml of tetrahydrofuran. The resulting orange solution was stirred at room temperature for 4 hours and then poured into a mixture of water and ether. The ether layer was separated, washed with water, and dried over magnesium sulfate. Evaporation of the solvent gave a crude brown oil. Flash column chromatography yielded 0.6 g (64% yield) of a yellow oil which was identified as being identical to the product of Example 2.

EXAMPLES 4–6 cis-jasmone

EXAMPLE 4

Precursor

Step A 10 g (100 millimole) of 4-methyl-3-pentene-2-one:

$$CH_3-C(CH_3)=CH-C(O)-CH_3$$

was dissolved in 500 ml of methylene chloride. 50 ml of water and 11 g (80 millimole) of calcium hypochlorite were added and the mixture cooled with ice. With rapid stirring, 6 g (1 equivalent) of glacial acetic acid was added dropwise over the course of 5 minutes. The cloudy mixture was stirred for another 20 minutes and then diluted with 100 ml of water. The organic layer was separated and washed sequentially with water (100 ml) and diluted sodium bicarbonate (100 ml). Drying over magnesium sulfate yielded a compound which was identified as 3-chloro-4-methyl-4-pentene-2-one:

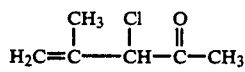

Step B 2 ml of hexamethylphosphoramide was added to a solution of 1.7 g (16 millimole) of potassium t-butoxide in 15 ml of tetrahydrofuran, and cooled to −70° C. under nitrogen. 2 g (15 millimole) of the product of Step A in 4 ml tetrahydrofuran was added over the course of 5 minutes, with stirring. The stirring of the deep orange solution was continued for another 15 minutes and then a solution of 3.5 g (15 millimole) of the tosylate of cis-2-pentene-1-ol in 2 ml tetrahydrofuran was added. After 30 minutes the mixture was warmed to 0° C., maintained at that temperature for 1 hour, and then warmed to room temperature, followed by the addition of 10 ml of 1N NH$_4$Cl. Following extraction with ether, 2.5 g of a crude, yellow-brown oil was obtained. Flash column chromatography yielded 1.1 g (16% yield) of 3-chloro-3-(cis-2-pentenyl)-4-methyl-4-pentene-2-one:

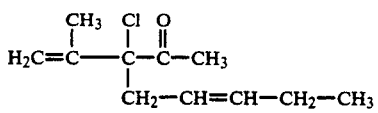

EXAMPLE 5

Invention 0.4 g (2.5 millimole) of the final product of Example 4 was dissolved in 1 ml of tetrahydrofuran. 20 ml of NH$_4$OH was added and the mixture was stirred for 12 hours. Dilution with water and extraction with ether produced a crude product which was purified by flash column chromatography to yield 0.3 g (73% yield) of 2-(cis-2-pentenyl)-3-methyl-2-cyclopenteneone (commonly known as cis-jasmone):

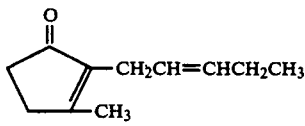

EXAMPLE 6

Invention 1.1 g (7.5 millimole) of the final product of Example 4 was dissolved in 10 ml of tetrahydrofuran. 50 mg of tetrabutyl ammonium bromide was added, and with rapid stirring, 2.4 ml (9 millimole) of 4N NaOH in 2 ml of tetrahydrofuran was added over a period of 3 minutes. The pale orange solution was stirred for another 4 hours and then diluted with water and extracted with ether. Evaporation of the ether followed by flash column chromatography of the residual oil yielded 0.7 g (71% yield of cis-jasmone.

EXAMPLES 7-8

2,3-dimethyl-2-cyclopentene-2-one

EXAMPLE 7

Precursor

Step A 2-methyl-2-butene was reacted with acetyl chloride using SnCl$_4$ as a catalyst to produce 3,4-dimethyl-3-pentene-2-one:

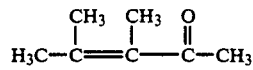

Step B 4.5 g (40 millimole) of the product of Step 4 was dissolved in 20 ml of water and 200 ml of dichloromethane, followed by the addition of 4 g (28 millimole) of calcium hypochlorite. The mixture was cooled to 0° C. and 2.8 g (42 millimole) of glacial acetic acid was added dropwise over 5 minutes. After waiting 20 minutes, the mixture was diluted with 50 ml of water. The organic layer was separated, washed with 20 ml of water and 20 ml of dilute NaHCO$_3$ solution, and dried over MgSO$_4$. Evaporation of the solvent yielded 4.8 g (82% yield) of a yellow oil identified as 3-chloro-3,4-dimethyl-4-pentene-2-one:

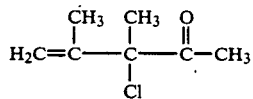

EXAMPLE 8

Invention 1.4 g (10 millimole) of the final product of Example 7 was dissolved in 10 ml of tetrahydrofuran. 100 mg of triethyl dodecyl ammonium chloride was added, and with stirring, a solution of 0.5 g (1 equivalent) of NaOH in 1 ml of water and 2 ml of tetrahydrofuran was added dropwise over 2 minutes. The resulting pale orange solution was then stirred for another 4 hours. Dilution with water, extraction with ether, and distillation yielded 1.0 g (88% yield) of 2,3-dimethyl-2-cyclopentene-1-one:

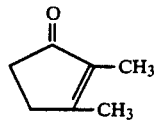

EXAMPLE 9 methyleneomycin-B

EXAMPLE 9

Post Invention Reaction

Generally following the procedure of Mikolajcayk et al, above, the product of Example 8 was hydroxymethylated and then dehydrated to yield 2,3-dimethyl-5-methylenyl-2-cyclopentene-1-one (commonly known as methylenomycin-B):

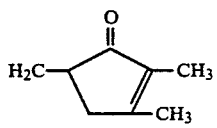

EXAMPLES 10–13 dihydrojasmone

EXAMPLE 10

Precursor

Step A 100 ml of liquid ammonia was condensed into a 2-neck flask fitted with a dropping funnel, inlet tube, and dry-ice condenser. A few crystals of ferric chloride were added, followed by the addition of 2.3 g (0.1 mole) of sodium. When the sodium was converted to sodium amide, the deep blue color changed to gray. A solution of 10 g (0.1 mole) of 4-methyl-3-pentene-2-one in 10 ml of ether was added dropwise, resulting in a green-blue solution. After 15 minutes a solution of 1.5 g (1 equivalent) of bromopentane in 5 ml of ether was added, changing the color to light brown. After 1 hour of stirring, the ammonia was allowed to evaporate and ether and water were added. The organic layer was separated, washed with water, washed with two 10 ml portions of 5% HCl, and dried over MgSO$_4$. Evaporation of the ether yielded 15 g (88% yield) of 3-pentyl-4-methyl-4-pentene-2-one:

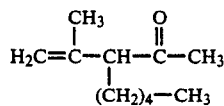

Step B

All of the product of Step B was mixed with 200 mg of p-toluenesulfonic acid and heated to a gentle reflux for 20 minutes. The red solution was cooled to room temperature and then chromatographed on silica gel to give 10 g (60% yield) of a yellow oil identified as 3-pentyl-4-methyl-3-pentene-2-one:

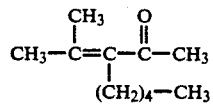

Step C 3.2 g (20 millimole) of calcium hypochlorite was added to a solution of 5.2 g (31 millimole) of the product of Step C in 160 ml of methylene chloride and 16 ml of water. The mixture was cooled to 0° C. and stirred rapidly while 2 ml (30 millimole) of glacial acetic acid was added dropwise over 5 minutes. After 20 minutes the cloudy mixture was diluted with 20 ml of water and the organic layer separated. Normal washing and evaporation yielded 5.8 g (92% yield) of a yellow-tan oil identified as 87% pure 3-chloro-3-pentyl-4-methyl-4-pentene-2-one:

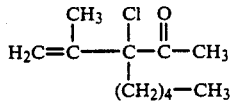

EXAMPLE 11

Invention 2 g (10 millimole) of the final product of Example 10 were dissolved in 1 ml of tetrahydrofuran and 50 ml of a 28% aqueous solution of NH$_4$OH was added with stirring. After 12 hours of stirring, the solution was diluted with 40 ml of water and extracted with two 20 ml portions of ether. Evaporation of the solvent followed by flash column chromatography yielded 1.3 g (81% yield) of a pale yellow oil identified as 2-pentyl-3-methyl-2-cyclopentene-1-one (commonly known as dihydrojasmone):

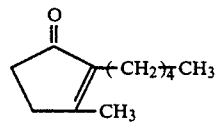

EXAMPLE 12

Invention

To a solution of 1.6 g (8 millimole) of the final product of Example 10 in 20 ml of tetrahydrofuran, 100 mg of triethyldodecylammonium chloride and a solution of 0.5 g (10 millimole) of sodium hydroxide in 1 ml of water and 2 ml of tetrahydrofuran were added. The resulting orange solution was stirred at room temperature for 6 hours, diluted with 10 ml of water, and extracted with ether. Evaporation of solvent followed by flash column chromatography gave 1.1 g (74% yield) of a colorless oil identified as dihydrojasmone.

EXAMPLE 13

Invention

A solution of 1 g (5 millimole) of the final product of Example 10 in 10 ml of tetrahydrofuran was added dropwise to a stirred solution of 0.6 g (6 millimole) of potassium t-butoxide in 1.5 ml of tetrahydrofuran at 20° C. The resulting deep orange brown solution was stirred at room temperature for 3 hours (thin layer chromatography monitoring showed that the starting material completely reacted after 2 hours). Dilution with water, extraction with ether, removal of solvent gave a brown oil which was purified by flash column chromatography on silica gel to yield 0.6 g (74% yield of a yellow oil identified as dihydrojasmone).

EXAMPLES 14–18

2-benzyl-3-methyl-2-cyclopentene-1-one

EXAMPLE 14

Precursor

Step A1

To stirred solution of 60 millimole of sodium amide (prepared from 1.4 g of sodium and 100 ml of NH$_3$) in ammonia, 6 g (60 millimole) of 4-methyl-3-pentene-2-one in 10 ml of ether was added dropwise. After 20 minutes, 7.8 g (61 millimole) of benzyl chloride in 2 ml of ether was added to the blue green solution, resulting in a pale green suspension. Stirring was continued for another hour and then the ammonia was allowed to evaporate while ether was added. The slurry was stirred with 25 ml of water and the organic layer separated. The extract was washed with 20 ml of 5% HCl and 20 ml of water, and then dried over magnesium sulfate. Evaporation gave 9 g (81% yield) of a crude yellow oil which was mixed with 200 mg of p-toluene sulfonic acid and gently refluxed for 20 minutes. The red brown solution was cooled to room temperature as purified by flash column chromatography to give 5.4 g (51% yield) of a deep yellow oil identified as 3-benzyl-4-methyl-3-pentene-2-one:

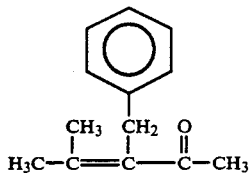

Step A2 (alternative to A1)

A solution of 2.7 g (65 millimole) of NaOH in 2.5 ml of water was added to 8.5 g (90 millimole) of 4-methyl-3-pentene-2-one and stirred at 40° C. while 200 mg of triethyldodecyl ammonium chloride was added. The red solution was treated with 5.4 g (45 millimole) of benzyl chloride and the stirring continued for 4 hours at 50° C. The resulting yellow brown solution was cooled to room temperature and diluted with 10 ml of water, followed by extraction with 50 ml of ether. The organic extract was washed with 10 ml of water, 10 ml of 10% HCl, and then another 10 ml of water, followed by drying over magnesium sulfate. Evaporation of solvent and flash column chromatography gave 4.4 g (52% yield) of 3-benzyl-4-methyl-3-pentene-2-one.

Step B

A stirred solution of 4.4 g (23 millimole) of the product of Step A in 100 ml of dichloromethane and 12 ml of water was cooled to 0° C. and then 2.3 g (16 millimole) of calcium hypochlorite was added, followed by the dropwise addition of 1.6 g (26.6 millimole of glacial acetic acid). The resulting cloudy solution was stirred (still at 0° C.) for 20 minutes and then diluted with 30 ml of water. Washing and extraction gave 4.6 g (89% yield) of a tan yellow oil identified as 3-benzyl-3-chloro-4-methyl-4-pentene-2-one:

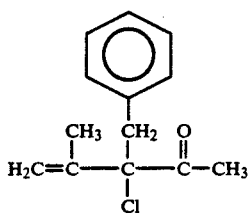

EXAMPLE 15

Invention 1 g (4.5 millimole) of the final product of Example 14 was contacted with $NH_4OH$ in the manner of the previous examples to yield 0.5 g (60% yield) of 2-benzyl-3-methyl-2-cyclopentene-1-one:

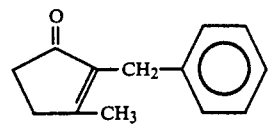

EXAMPLE 16

Invention

A solution of 0.21 g (5 millimole) of NaOH in 0.4 ml of water and 2 ml of tetrahydrofuran was added to a solution of 1 g (4.6 millimole) of the final product of Example 14 in 20 ml of tetrahydrofuran. 100 mg of triethyldodecyl ammonium chloride was added and the mixture stirred for 3 hours. Washing, extraction, and chromatographic sparation produced 0.8 g (92% yield) of 2-benzyl-3-methyl-2-cyclopentene-1-one.

EXAMPLE 17

Invention

A solution of 2.2 g (10 millimole) of the final product of Example 14 in 5 ml of tetrahydrofuran was slowly added to a solution of 1.2 g (10 millimole) of potassium t-butoxide in 20 ml of tetrahydrofuran at 20° C. The resulting red brown solution was stirred at room temperature for 2 hours. Washing, extraction, and flash column chromatography gave 1.7 g (54% yield) of 2-benzyl-3-methyl-2-cyclopentene-1-one.

EXAMPLE 18

Invention 4 ml (10 millimole) of 2.5 molar n-butyl lithium was added to a stirred solution of 1 g (10 millimole) of di-isopropyl amine in 10 ml of tetrahydrofuran at 0° C. under a nitrogen blanket. After 30 minutes the solution was cooled to $-70°$ C. and a solution of 2.2 g (9.8 millimole) of the final product of Example 14 in 10 ml of tetrahydrofuran was added dropwise over a period of 10 minutes. The yellow orange solution was then warmed to room temperature over the course of 1 hour (thin layer chromatography showed that the reaction took place above 0° C.). After 20 minutes, the orange yellow solution was quenched with 5 ml of 1N $NH_4Cl$ and extracted with two 20 ml portions of ether. The ether extract was washed with two 10 ml portions of water and was dried over $MgSO_4$. Evaporation of the ether yielded 2 g of a brown oil. Flash column chromatography gave 0.5 g (52% yield) of 2-benzyl-3-methyl-2-cyclopentene-1-one.

What is claimed is:

1. A method of preparing a cyclopentenone compound of the formula:

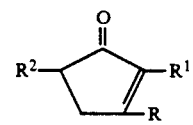

comprising bringing into reactive contact a. a penteneone of the formula:

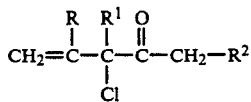

wherein R and $R^1$ are each independently alkyl, alkenyl, or aryl radicals having 1 to 32 carbon atoms and $R^2$ is H or a $C_1$ to $C_{12}$ hydrocarbon moiety; with
   b. a strong base.
2. The method of claim 1 wherein R is alkyl or alkenyl and $R^1$ is alkyl, alkenyl, or aryl.
3. The method of claim 2 wherein R is alkyl and $R^1$ is alkyl or alkenyl.
4. The method of claim 3 wherein R and $R^1$ each independently have 1 to 8 carbon atoms.
5. The method of claim 3 wherein R is methyl.
6. The method of claim 5 wherein $R^1$ is methyl, pentyl, or cis-2-pentenyl.
7. The method of claim 1 wherein $R^2$ has 1 to 12 carbon atoms.
8. The method of claim 7 wherein $R^2$ has 1 to 6 carbon atoms.
9. The method of claim 8 wherein $R^2$ is ethyl.
10. The method of claim 1 wherein said contacting takes place from 0° C. to 100° C.
11. The method of claim 1 wherein said strong base is
   a. $NH_4OH$;
   b. an alkali metal hydroxide in combination with a phase transfer catalyst;
   c. an alkali metal alkoxide; or
   d. an alkyl lithium amine.
12. The method of claim 11 wherein said strong base is $NH_4OH$.
13. The method of claim 11 wherein the strong base is an alkali metal hydroxide in combination with a phase transfer catalyst.
14. The method of claim 13 wherein said alkali metal hydroxide is NaOH.
15. The method of claim 14 wherein said phase transfer catalyst is triethyldodecyl ammonium chloride.
16. The method of claim 11 wherein said strong base is an alkali metal alkoxide.
17. The method of claim 16 wherein said alkali metal alkoxide is potassium t-butoxide.
18. The method of claim 11 wherein said strong base is an alkyl lithium amine.
19. The method of claim 18 wherein said alkyl lithium amine is the in situ reaction product of an alkyl amine and an alkyl lithium compound.
20. The method of claim 19 wherein the alkyl amine is di-isopropyl amine and the alkyl lithium compound is n-butyl lithium.
21. The method of claim 11 wherein said strong base is used in an equivalent amount.

* * * * *